United States Patent
Xiao

(10) Patent No.: US 8,742,225 B2
(45) Date of Patent: Jun. 3, 2014

(54) COTTON VARIETY ST 5288B2F

(75) Inventor: Jinhua Xiao, St. Louis, MO (US)

(73) Assignee: Bayer CropScience LP, Research Triangle Park, NC (US)

( * ) Notice: Subject to any disclaimer, the term of this patent is extended or adjusted under 35 U.S.C. 154(b) by 185 days.

(21) Appl. No.: 12/906,599

(22) Filed: Oct. 18, 2010

(65) Prior Publication Data

US 2011/0093968 A1 Apr. 21, 2011

Related U.S. Application Data

(60) Provisional application No. 61/252,823, filed on Oct. 19, 2009.

(51) Int. Cl.
| | |
|---|---|
| *A01H 5/00* | (2006.01) |
| *A01H 5/10* | (2006.01) |
| *A01H 1/02* | (2006.01) |
| *A01H 4/00* | (2006.01) |
| *C12N 15/82* | (2006.01) |

(52) U.S. Cl.
USPC ........... 800/314; 800/265; 800/274; 800/278; 800/300; 800/302; 435/427

(58) Field of Classification Search
None
See application file for complete search history.

(56) References Cited

U.S. PATENT DOCUMENTS

2006/0191046 A1* 8/2006 Reid et al. ............... 800/314
2010/0107273 A1* 4/2010 Balducchi ............... 800/263

* cited by examiner

*Primary Examiner* — David T Fox

(57) ABSTRACT

The cotton variety ST 5288B2F is disclosed. The invention relates to seeds, plants, plant cells, plant tissue, harvested products and cotton lint as well as to hybrid cotton plants and seeds obtained by repeatedly crossing plants of variety ST 5288B2F with other plants. The invention also relates to plants and varieties produced by the method of essential derivation from plants of ST 5288B2F and to plants of ST 5288B2F reproduced by vegetative methods, including but not limited to tissue culture of regenerable cells or tissue from ST 5288B2F.

17 Claims, No Drawings

COTTON VARIETY ST 5288B2F

This application claims benefit under 35 U.S.C. 111(e) of provisional application No. 61/252,823 filed 19 Oct. 2009.

BACKGROUND OF THE INVENTION (i) Field of the Invention

This invention relates to the field of plant breeding. More particularly, the invention relates to a variety of cotton designated as ST 5288B2F, its essentially derived varieties and the hybrid varieties obtained by crossing ST 5288B2F as a parent line with plants of other varieties or parent lines.

(ii) Description of Related Art

Cotton is an important, fiber producing crop. Due to the importance of cotton to the textile industry, cotton breeders are increasingly seeking to obtain healthy, good yielding crops of excellent quality.

Cotton is commonly reproduced by self-pollination and fertilization. This type of sexual reproduction facilitates the preservation of plant and variety characteristics during breeding and seed production. The preservation of these characteristics is often important to plant breeders for producing cotton plants having desired traits. Other methods of producing cotton plants having desired traits are also used and include methods such as genetic transformation via *Agrobacterium* infection or direct transfer by microparticle bombardment. Examples of such methods are disclosed, for example, in U.S. Pub. No. 20090049564, incorporated by reference herein in its entirety.

Due to the environment, the complexity of the structure of genes and location of a gene in the genome, among other factors, it is difficult to predict the phenotypic expression of a particular genotype. In addition, a plant breeder may only apply his skills on the phenotype and not, or in a very limited way, on the level of the genotype. As a result, a particular plant breeder cannot breed the same variety twice using the same parents and the same methodology. Thus, a newly bred variety is an unexpected result of the breeding process. Indeed, each variety contains a unique combination of characteristics.

By carefully choosing the breeding parents, the breeding and selection methods, the testing layout and testing locations, the breeder may breed a particular variety type. In addition, a new variety may be tested in special comparative trials with other existing varieties in order to determine whether the new variety meets the required expectations.

SUMMARY OF THE INVENTION

The invention relates to seeds, plants, plant cells, parts of plants, cotton lint or fiber, and cotton textiles of cotton variety ST 5288B2F as well as to hybrid cotton plants and seeds obtained by repeatedly crossing plants of ST 5288B2F with other cotton plants. The invention encompasses plants and plant varieties produced by the method of derivation or essential derivation from plants of ST 5288B2F and to plants of ST 5288B2F reproduced by vegetative methods, including but not limited to regeneration of embryogenic cells or tissue of ST 5288B2F. The invention also encompasses methods of producing cotton seeds that comprise crossing plants of cotton variety ST 5288B2F either with itself or with a second, distinct cotton plant.

DETAILED DESCRIPTION OF THE INVENTION

The invention has been obtained by a general breeding process comprising the steps outlined below. For reference, see chapter 11, "Breeding Self-Pollinated Crops by Hybridization and Pedigree Selection" in Briggs and Knowles (1967).

Parent plants, which have been selected for good agronomic and fiber quality traits are manually crossed in different combinations. The resulting F1 (Filial generation 1) plants are self fertilized and the resulting F2 generation plants, which show a large variability on account of optimal gene segregation, are planted in a selection field.

These F2 plants are observed during the growing season for health, growth vigor, plant type, plant structure, leaf type, stand ability, flowering, maturity, seed yield, boll type, boll distribution, boll size, fiber yield and fiber quality. Plants are then selected. The selected plants are harvested and the bolls analyzed for fiber characteristics and the seed cleaned and stored. This procedure is repeated in the following growing seasons, whereby the selection and testing units increase from individual plants in the F2, to multiple plant containing 'lines' (descending from one mother plant) in the F5 and the number of units decrease from approximately 2500 plants in the F2 to 20 lines in the F5 by selecting about 10-20% of the units in each selection cycle.

The increased size of the units, whereby more seed per unit is available, allows the selection and testing in replicated trials on more than one location with a different environment and a more extensive and accurate analyzing of the fiber quality.

The lines or candidate varieties become genotypically more homozygous and phenotypically more homogeneous by selecting similar plant types within a line and by discarding the so called off-types from the very variable F2 generation on to the final F7 or F8 generation.

Depending on the intermediate results the plant breeder may decide to vary the procedure described above, such as by accelerating the process by testing a particular line earlier or retesting a line another year. He may also select plants for further crossing with existing parent plants or with other plants resulting from the current selection procedure.

By the method of recurrent backcrossing, as described by Briggs and Knowles, supra, in chapter 13, "The Backcross Method of Breeding", the breeder may introduce a specific trait or traits into an existing valuable line or variety, while otherwise preserving the unique combination of characteristics of this line or variety. In this crossing method, the valuable parent is recurrently used to cross it at least two or three times with each resulting backcross F1, followed by selection of the recurrent parent plant type, until the phenotype of the resulting F1 is similar or almost identical to the phenotype of the recurrent parent with the addition of the expression of the desired trait or traits.

This method of recurrent backcrossing eventually results in an essentially derived variety, which is predominantly derived from the recurrent parent or initial variety. This method can therefore also be used to get as close as possible to the genetic composition of an existing successful variety. Thus, compared to the recurrent parent the essentially derived variety retains a distinctive trait, which can be any phenotypic trait, with the intention to profit from the qualities of that successful initial variety.

Depending on the number of backcrosses and the efficacy of the selection of the recurrent parent plant type and genotype, which can be supported by the use of molecular markers as described by P. Stam (2003), the genetic conformity with the initial variety of the resulting essentially derived variety may vary between 90% and 100%.

Other than recurrent backcrossing, as described herein, such essentially derived variety may also be obtained by the selection from an initial variety of an induced or natural occurring mutant plant, or of an occurring variant (off-type) plant, or of a somaclonal variant plant, or by genetic transformation of regenerable plant tissue or embryogenic cell cultures of the said initial variety by methods well known to those skilled in the art, such as Agrobacterium-mediated transformation as described by Sakhanokho et al, (2004), Reynaerts et al. (2000), Umbeck et al. (1988) and others. Examples of transgenic events transformed in this way are "LLCotton25," USDA-APHIS petition 02-042-01p, "Cot 102," USDA-APHIS petition 03-155-01p, and "281-24-236," USDA-APHIS petition 03-036-01p combined with "3006-210-23," USDA-APHIS petition 03-036-02p. Information regarding these and other transgenic events referred to herein may be found at the U.S. Department of Agriculture's (USDA) Animal and Plant Health Inspection Service (APHIS) website. An "Event" is defined as a (artificial) genetic locus that, as a result of genetic engineering, carries a foreign DNA comprising at least one copy of the gene(s) of interest. Other methods of genetic transformation are well known in the art such as microprojectile bombardment. See, e.g., U.S. Publication No. 20090049564, which is incorporated by reference herein in its entirety.

The plants selected or transformed retain the unique combination of the characteristics of ST 5288B2F, except for the characteristics (e.g., one, two, three, four or five characteristics) changed by the selection of the mutant or variant plant or by the addition of a desired trait via genetic transformation. Therefore, the product of essential derivation (i.e., an essentially derived variety), has the phenotypic characteristics of the initial variety, except for the characteristics that change as a result of the act of derivation. Plants of the essentially derived variety can be used to repeat the process of essential derivation. The result of this process is also a variety essentially derived from said initial variety.

In one embodiment, ST 5288B2F progeny plants are produced by crossing plants of ST 5288B2F with other, different or distinct cotton plants, and further selfing or crossing these progeny plants with other, distinct plants and subsequent selection of derived progeny plants. The process of crossing ST 5288B2F derived progeny plants with itself or other distinct cotton plants and the subsequent selection in the resulting progenies can be repeated up to 7 or 8 times in order to produce ST 5288B2F derived cotton plants.

ST 5288B2F is a BC3 derived line from a backcross-breeding program with 669AD-295-049 as the recurrent parent and an experimental line as the donor. The donor was a backcross derived line using SG125 as the recurrent parent and a B2RF line designated as GH_59910 as the donor. 669AD-295-049 is a backcross derived line using NuCotn 33B as the recurrent parent and GB669 (G. barbadense) as the donor. ST 5288B2F was evaluated in replicated agronomic trials to evaluate yield and fiber traits.

Data gathered from beltwide 2007 and 2008 replicated testing and purity evaluations indicated statistically similar yield performance to ST 5458B2RF. However, ST 5288B2F has statistically decreased fiber strength.

The variety will be maintained through pure line maintenance of breeder seed and production of foundation and registered classes of seed.

ST 5288B2F has been evaluated in many environments from 2007 and 2008 across the cotton belt by the staff of Bayer CropScience and many public researchers. No off-types were detected and no variants were noted in the variety. ST 5288B2F is considered to be uniform and stable.

Provided herein as embodiments of the invention are seeds, plants, plant cells and parts of plants of the cotton variety ST 5288B2F. Representative seeds of this variety were deposited under rule 37CFR 1.809, prior to issuance of a patent. Applicant made a deposit of at least 2500 seeds of cotton variety ST 5288B2F disclosed herein. This deposit was made on Sep. 11, 2013 with the American Type Culture Collection (ATCC), 10801 University Boulevard, Manassas, Va. 20110-2209 USA. The accession number for the deposit is ATCC Accession No. PTA-120587. Access to this deposit will be available during the pendency of the application to the Commissioner of Patents and Trademarks and persons determined by the Commissioner to be entitled thereto upon request. The deposit will be maintained for a period of 30 years, or 5 years after the most recent request, or for the enforceable life of the patent, whichever is longer, and will be replaced if it becomes nonviable during that period. Upon allowance of any claims in the application, the Applicants will make available to the public, pursuant to 37 C.F.R. §1.808, sample(s) of the deposit with the ATCC Applicant does not waive any rights granted under this patent or under the Plant Variety Protection Act (7 U.S.C. 2321 et seq.).

Plants produced by growing such seeds are provided herein as embodiments of the invention. Also provided herein are pollen or ovules of these plants, as well as a cell or tissue culture of regenerable cells from such plants. In another embodiment, the invention provides for a cotton plant regenerated from such cell or tissue culture, wherein the regenerated plant has the morphological and physiological characteristics of cotton cultivar ST 5288B2F, as described herein (e.g., Table 1), when grown in the same environmental conditions. In yet another embodiment, the invention provides methods of testing for a plant having the morphological and physiological characteristics of cotton cultivar ST 5288B2F. In one embodiment, the testing for a plant having the morphological and physiological characteristics of cotton cultivar ST 5288B2F is performed in the same field, under the same conditions and in the presence of plants of ST 5288B2F, e.g., plants grown from the deposited seed. In another embodiment, the characteristics to be tested for are those described herein (e.g., Table 1).

In another embodiment, the present invention provides regenerable cells for use in tissue culture of cotton cultivar ST 5288B2F. The tissue culture will preferably be capable of regenerating plants having the physiological and morphological characteristics of the cotton cultivar ST 5288B2F, and of regenerating plants having substantially the same genotype as the cotton plant of the present invention. Preferably, the regenerable cells in such tissue cultures will be from embryos, protoplasts, meristematic cells, callus, pollen, leaves, anthers, pistils, roots, root tips, flowers, seeds, pods or stems. Still further, the present invention provides cotton plants regenerated from the tissue cultures of the invention.

Yet another aspect of the current invention is a cotton plant of the cotton variety ST 5288B2F comprising at least a first transgene, wherein the cotton plant is otherwise capable of expressing all the physiological and morphological characteristics of the cotton variety ST 5288B2F. In particular embodiments of the invention, a plant is provided that comprises a single locus conversion. A single locus conversion may comprise a transgenic gene which has been introduced by genetic transformation into the cotton variety ST 5288B2F or a progenitor thereof. A transgenic or non-transgenic single locus conversion can also be introduced by backcrossing, as is well known in the art. In certain embodiments of the invention, the single locus conversion may comprise a dominant or recessive allele. The locus conversion may confer potentially any desired trait upon the plant as described herein.

Single locus conversions may be implemented by a plant breeding technique called backcrossing wherein essentially all of the desired morphological and physiological characteristics of a variety are recovered in addition to the characteristics conferred by the single locus transferred into the variety via the backcrossing technique. A single locus may comprise one gene, or in the case of transgenic plants, one or more transgenes integrated into the host genome at a single site (locus).

In a particular aspect, the invention provides for a method of introducing a single locus conversion into cotton cultivar ST 5288B2F comprising: (a) crossing the ST 5288B2F plants, grown from deposited seed with plants of another cotton line that comprise a desired single locus to produce F1 progeny plants; (b) selecting F1 progeny plants that have the single locus to produce selected F1 progeny plants; (c) crossing the selected F1 progeny plants with the ST 5288B2F plants to produce first backcross progeny plants; (d) selecting for first backcross progeny plants that have the desired single locus and the physiological and morphological characteristics of cotton cultivar ST 5288B2F as described herein (e.g., Table 12), when grown in the same environmental conditions, to produce selected first backcross progeny plants; and (e) repeating steps (c) and (d) one or more times (e.g. one, two, three, four, etc. times) in succession to produce selected third or higher backcross progeny plants that comprise the desired single locus and all of the physiological and morphological characteristics of cotton cultivar ST 5288B2F as described herein (e.g., Table 12), when grown in the same environmental conditions. Plants produced by this method have all of the physiological and morphological characteristics of ST 5288B2F, except for the characteristics derived from the desired trait.

Another embodiment of the invention provides for a method of producing an essentially derived plant of cotton variety ST 5288B2F comprising introducing a transgene conferring the desired trait into the plant, resulting in a plant with the desired trait and all of the physiological and morphological characteristics of cotton variety ST 5288B2F when grown in the same environmental conditions. In another embodiment, the invention provides for a method of producing an essentially derived cotton plant from ST 5288B2F comprising genetically transforming a desired trait in regenerable cell or tissue culture from a plant produced by the invention, resulting in an essentially derived cotton plant that retains the expression of the phenotypic characteristics of cotton variety ST 5288B2F, except for the characteristics changed by the introduction of the desired trait.

Desired traits described herein include but are not limited to modified cotton fiber characteristics, herbicide resistance, insect or pest resistance, disease resistance, including bacterial or fungal disease resistance, male sterility, modified carbohydrate metabolism and modified fatty acid metabolism. Such traits and genes conferring such traits are known in the art. See, e.g., US 20090049564, incorporated by reference herein in its entirety.

The invention also provides for methods wherein the desired trait is herbicide tolerance and the tolerance is linked to a herbicide such as glyphosate, glufosinate, sulfonylurea, dicamba, phenoxy proprionic acid, cyclohexanedione, triazine, benzonitrile, bromoxynil or imidazalinone. The invention also provides for methods wherein the herbicide tolerance is an expression of the Event "LLCotton25" and the insect resistance is an expression of the Event "281-24-236", Event "3006-210-23" or a combination thereof, or Event "Cot 102".

In one embodiment, the desired trait is insect resistance conferred by a transgene encoding a *Bacillus thuringiensis* (*Bt*) endotoxin, a derivative thereof, or a synthetic polypeptide modeled thereon.

Also included herein is a method of producing cotton seed, comprising the steps of using the plant grown from seed of cotton variety ST 5288B2F, of which a representative seed sample will be deposited as a recurrent parent in crosses with other cotton plants different from ST 5288B2F, and harvesting the resultant cotton seed.

Another embodiment of this invention relates to seeds, plants, plant cells and parts of plants of cotton varieties that are essentially derived from ST 5288B2F, being essentially the same as this invention by expressing the unique combination of characteristics of ST 5288B2F, including the herbicide and insect resistance of ST 5288B2F, except for the characteristics (e.g., one, two, three, four, or five, characteristics) being different from the characteristics of ST 5288B2F as a result of the act of derivation.

Another embodiment of this invention is the reproduction of plants of ST 5288B2F by the method of tissue culture from any regenerable plant tissue obtained from plants of this invention. Plants reproduced by this method express the specific combination of characteristics of this invention and fall within its scope. During one of the steps of the reproduction process via tissue culture, somaclonal variant plants may occur. These plants can be selected as being distinct from this invention, but still fall within the scope of this invention as being essentially derived from this invention.

Another embodiment of the invention provides for a method of producing an inbred cotton plant derived from the cotton variety ST 5288B2F comprising: (a) preparing a progeny plant derived from cotton variety ST 5288B2F, a representative sample of seed of said variety will be deposited by crossing cotton variety ST 5288B2F with a cotton plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional 3-10 generations with sufficient inbreeding to produce an inbred cotton plant derived from the cotton variety ST 5288B2F.

Another embodiment of this invention is the production of a hybrid variety, comprising repeatedly crossing plants of ST 5288B2F with plants of a different variety or varieties or with plants of a non-released line or lines. In practice, three different types of hybrid varieties may be produced (see e.g., Chapter 18, "Hybrid Varieties" in Briggs and Knowles, supra):

The "single cross hybrid" produced by two different lines, the "three way hybrid", produced by three different lines such that first the single hybrid is produced by using two out of the three lines followed by crossing this single hybrid with the third line, and the "four way hybrid" produced by four different lines such that first two single hybrids are produced using the lines two by two, followed by crossing the two single hybrids so produced.

Each single, three way or four way hybrid variety so produced and using ST 5288B2F as one of the parent lines contains an essential contribution of ST 5288B2F to the resulting hybrid variety and falls within the scope of this invention.

The invention also provides for cotton lint or fiber produced by the plants of the invention, plants reproduced from the invention, and plants essentially derived from the invention. The final textile produced from the unique fiber of ST 5288B2F also falls within the scope of this invention. The invention also provides for a method of producing a commodity plant product (e.g., lint, cotton seed oil) comprising obtaining a plant of the invention or a part thereof, and producing said commodity plant product therefrom.

The entire disclosure of each document cited herein (e.g., US patent publications, non-patent literature, etc.) is hereby incorporated by reference.

EXAMPLE

Characterization of Cotton Variety ST 5288B2F

Seeds of the variety ST 5288B2F, of which a representative sample will be deposited, were planted, together with seeds of cotton variety ST 5458B2F as reference variety, in field trials at two locations: Stoneville, Miss. and Clarkdale, Ark. ST 5288B2F has an indeterminate plant growth habit and has a strong erect central stem. ST 5288B2F is most similar to ST 5458B2F. However, ST 5288B2F has statistically decreased fiber strength when compared with ST 5458B2F (see Table 1, 2 and 3).

Analysis of variance procedures were used to obtain least significant difference at the 5% level, using a commercially available software licensed under the name Prism.

References to other statistically significant differences in fiber properties between the varieties are presented in Table 4.

General descriptions of morphological characteristics including, leaf, stem, gland, flower, plant height, and nodes to first fruiting branch, were collected from 10 plants in each of three replications and are represented in Table 5.

DEPOSIT INFORMATION

Applicant made a deposit of at least 2500 seeds of cotton variety ST 5288B2F disclosed herein. This deposit was made on Sep. 11, 2013 with the American Type Culture Collection (ATCC), 10801 University Boulevard, Manassas, Va. 20110-2209 USA. The accession number for the deposit is ATCC Accession No. PTA-120587. Access to this deposit will be available during the pendency of the application to the Commissioner of Patents and Trademarks and persons determined by the Commissioner to be entitled thereto upon request. The deposit will be maintained for a period of 30 years, or 5 years after the most recent request, or for the enforceable life of the patent, whichever is longer, and will be replaced if it becomes nonviable during that period. Upon allowance of any claims in the application, the Applicants will make available to the public, pursuant to 37 C.F.R. §1.808, sample(s) of the deposit with the ATCC. Applicant does not waive any rights granted under this patent or under the Plant Variety Protection Act (7 U.S.C. 2321 et seq.).

DEFINITIONS

In the description and tables which follow, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Cm to FFB: Measure of centimeters to first fruiting branch.

Crossing: The mating of two parent plants.

Cross-pollination: Fertilization by the union of two gametes from different plants.

Desired Agronomic Characteristics: Agronomic characteristics (which will vary from crop to crop and plant to plant) such as yield, maturity, pest resistance and lint percent which are desired in a commercially acceptable crop or plant. For example, improved agronomic characteristics for cotton include yield, maturity, fiber content and fiber qualities.

Diploid: A cell or organism having two sets of chromosomes.

Disease Resistance: The ability of plants to restrict the activities of a specified pest, such as an insect, fungus, virus, or bacterial.

Disease Tolerance: The ability of plants to endure a specified pest (such as an insect, fungus, virus or bacteria) or an adverse environmental condition and still perform and produce in spite of this disorder.

Donor Parent: The parent of a variety which contains the gene or trait of interest which is desired to be introduced into a second variety.

E1: Refers to elongation, a measure of fiber elasticity (high=more elastic).

Emasculate: The removal of plant male sex organs or the inactivation of the organs with a cytoplasmic or nuclear genetic factor conferring male sterility or a chemical agent.

Essentially all the physiological and morphological characteristics: A plant having essentially all the physiological and morphological characteristics means a plant having the physiological and morphological characteristics, except for the characteristics derived from the desired trait.

$F_1$ Hybrid: The first generation progeny of the cross of two nonisogenic plants.

Fallout (Fo): As used herein, the term "fallout" refers to the rating of how much cotton has fallen on the ground at harvest.

FB5 cm to FFN: Measure of centimeters from main stem to first fruiting node at fruiting branch 5.

2.5% Fiber Span Length: Refers to the longest 2.5% of a bundle of fibers expressed in inches as measured by a digital fibergraph.

Fiber Characteristics: Refers to fiber qualities such as strength, fiber length, micronaire, fiber elongation, uniformity of fiber and amount of fiber.

Fiber Elongation: Sometimes referred to as E1, refers to the elongation of the fiber at the point of breakage in the strength determination as measured by High Volume Instrumentation (HVI).

Fiber Span Length: The distance spanned by a specific percentage of fibers in a test specimen, where the initial starting point of the scanning in the test is considered 100 percent as measured by a digital fibergraph.

Fiber Strength (Str): Denotes the force required to break a bundle of fibers. Fiber strength is expressed in grams per tex on an HVI.

Fruiting Nodes: The number of nodes on the main stem from which arise branches that bear fruit or boll in the first position.

Genotype: The genetic constitution of a cell or organism.

Gin Turnout: Refers to fraction of lint in a machine harvested sample of seed cotton (lint, seed, and trash).

Haploid: A cell or organism having one set of the two sets of chromosomes in a diploid.

Length (Len): The fiber length in inches using an HVI.

Linkage: A phenomenon wherein alleles on the same chromosome tend to segregate together more often than expected by chance if their transmission was independent.

Lint Index: The weight of lint per seed in milligrams.

Lint Percent: The percentage of the seed cotton that is lint, handpicked samples.

Lint Yield: Refers to the measure of the quantity of fiber produced on a given unit of land. Presented below in pounds of lint per acre.

Lint/boll: As used herein, the term "lint/boll" is the weight of lint per boll.

Maturity Rating: A visual rating near harvest on the amount of open boils on the plant. The rating range is from 1 to 5, 1 being early and 5 being late.

Micronaire (Mic): Refers to a measure of fiber fineness (high=coarse fiber) as measured with an HVI machine. Within a cotton cultivar, micronaire is also a measure of maturity. Micronaire differences are governed by changes in perimeter or in cell wall thickness, or by changes in both. Within a variety, cotton perimeter is fairly consistent and maturity will cause a change in micronaire. Consequently, micronaire has a high correlation with maturity within a variety of cotton. Maturity is the degree of development of cell wall thickness.

Mr: Fiber maturity ratio.

Phenotype: The detectable characteristics of a cell or organism, which characteristics are the manifestation of gene expression.

Plant Height: The average height in meters of a group of plants.

Quantitative Trait Loci (QTL): Quantitative trait loci (QTL) refer to genetic loci that control to some degree numerically representable traits that are usually continuously distributed.

Recurrent Parent: The repeating parent (variety) in a backcross breeding program. The recurrent parent is the variety into which a gene or trait is desired to be introduced.

Regeneration: The development of a plant from tissue culture.

Seed/boll: Refers to the number of seeds per boll, handpicked samples.

Seedcotton/boll: Refers to the weight of seedcotton per boll, handpicked samples.

Seedweight: Refers to the weight of 100 seeds in grams.

Self-pollination: The transfer of pollen from the anther to the stigma of the same plant or a plant of the same genotype.

Single Locus Converted (Conversion) Plant: Plants which are developed by a plant breeding technique called backcrossing wherein essentially all of the desired morphological and physiological characteristics of a variety are recovered in addition to the characteristics conferred by the single locus transferred into the variety via the backcrossing technique. A single locus may comprise one gene, or in the case of transgenic plants, one or more transgenes integrated into the host genome at a single site (locus).

Stringout Rating: also sometimes referred to as "Storm Resistance" refers to a visual rating prior to harvest of the relative looseness of the seed cotton held in the boll structure on the plant. The rating values are from 1 to 5 (tight to loose in the boll).

Substantially Equivalent: A characteristic that, when compared, does not show a statistically significant difference (e.g., p=0.05) from the mean.

T1: A measure of fiber strength, grams per tex (high=stronger fiber).

Tissue Culture: A composition comprising isolated cells of the same or a different type or a collection of such cells organized into parts of a plant.

Transgene: A genetic locus comprising a sequence which has been introduced into the genome of a cotton plant by transformation.

Uniformity Ratio (Ur): The proportion of uniform length fibers. The uniformity ratio is determined by dividing the 50% fiber span length by the 2.5% fiber span length.

Vegetative Nodes: The number of nodes from the cotyledonary node to the first fruiting branch on the main stem of the plant.

TABLE 1

Fiber strength (Str). Data from 2007 RCB in Stoneville, MS.

| Entry | Str |
|---|---|
| ST 5288B2F | 29.8 |
| ST 5458B2F | 33.4 |
| LSD(.05) | 2.4 |
| CV | 3.8 |
| # Reps | 2 |

TABLE 2

Fiber strength (Str). Data from 2008 RCB in Clarkdale, AR.

| Entry | Str |
|---|---|
| ST 5458B2F | 31.8 |
| ST 5288B2F | 28.2 |
| LSD(.05) | 2.3 |
| CV | 3.7 |
| # Reps | 2 |

TABLE 3

Fiber strength (Str). Data from 2008 RCB in Stoneville, MS.

| Entry | Str |
|---|---|
| ST 5288B2F | 29.2 |
| ST 5458B2F | 34.7 |
| LSD(.05) | 1.8 |
| CV | 2.8 |
| # Reps | 2 |

TABLE 4

Fiber characteristics. Data from 2007 and 2008 Beltwide* trials.

| Entry | Yield | Lint % | Len | Str | Mic | UR | Elong | Mat |
|---|---|---|---|---|---|---|---|---|
| ST 5458B2F | 1686 | 0.41 | 1.12 | 30.1 | 4.6 | 81.1 | 9.9 | 57.5 |
| ST 5288B2F | 1667 | 0.43 | 1.12 | 28.3 | 4.5 | 81.7 | 10.3 | 59.3 |
| LSD(.05) | 39 | 0.00 | 0.01 | 0.3 | 0.1 | 0.6 | 0.1 | 2.1 |
| CV | 6.1 | 2.5 | 2.6 | 2.56 | 3.4 | 2.3 | 5.5 | 7 |
| Sig. | 0.63 | 0.00 | 0.53 | 0.00 | 0.08 | 0.15 | 0.00 | 0.28 |
| # Locs | 44 | 44 | 45 | 45 | 45 | 45 | 45 | 34 |

*# Locs per region: Mid-Atlantic-10, Lower Southeast-9, MidSouth-11, TX Plains-10, Soutwest-4.

TABLE 5

General description of morphological characteristics

| | | Variety | |
|---|---|---|---|
| description of characteristic | possible expression/note | ST 5288B2F | ST 5458B2F |
| General Plant Type | | | |
| Plant Habit | spreading, intermediate, compact | Intermediate | Intermediate |
| Foliage | sparse, intermediate, dense | Intermediate | Intermediate |
| Stem Lodging | lodging, intermediate, erect | Erect | Erect |
| Fruiting Branch | clustered, short, normal | Normal | Normal |
| Growth | determinate, intermediate, indeterminate | Indeterminate | Indeterminate |
| Leaf color | greenish yellow, light green, medium green, dark green | Light Green | Light Green |
| Boll Shape | Length < Width, L = W, L > W | Length > Width | Length > Width |
| Boll Breadth | broadest at base, broadest at middle | Middle | Middle |
| Maturity | date of 50% open bolls | | |
| Plant | | | |
| cm. to first Fruiting Branch | from cotyledonary node | 13.50 | 15.50 |
| No. of nodes to 1st Fruiting Branch | excluding cotyledonary node | 7 | 7.8 |
| Mature Plant Height in cm. | cotyledonary node to terminal | | |
| Leaf: upper most, fully expanded leaf | | | |
| Type | normal, sub-okra, okra, super-okra | Normal | Normal |
| Pubescense | absent, sparse, medium, dense | Dense | Dense |
| Nectaries | present, absent | Present | Present |
| Stem Pubescense | glabrous, intermediate, hairy | Hairy | Intermediate |
| Glands (Gossypol) | absent, sparse, normal, more than normal | | |
| Leaf | | Normal | Normal |
| Stem | | Normal | Normal |
| Calyx lobe | (normal is absent) | Normal | Normal |
| Flower | | | |
| Petals | cream, yellow | Cream | Cream |
| Pollen | cream, yellow | Cream | Cream |
| Petal Spot | present, absent | Absent | Absent |
| Seed | | | |
| Seed Index | g/100 seed fuzzy basis | 8.6 | 9.6 |
| Lint Index | g lint/100 seeds | 15.4 | 16.5 |
| Boll | | | |
| Lint percent, picked | | 43.0 | 41.0 |
| Gin Turnout, stripped | | | |
| Number of Seeds per Boll | | 36 | 33 |
| Grams Seed Cotton per Boll | | 8.64 | 8.6 |
| Number of Locules per Boll | | 4 | 4 |
| Boll Type | storm proof, storm resistant, open | Open | Open |
| Fiber Properties | | | |
| Method HVI | | | |
| Length, inches, 2.5% SL | | 1.12 | 1.12 |
| Uniformity (%) | | 81.7 | 81.1 |
| Strength, T1 (g/tex) | | 28.3 | 30.1 |
| Elongation, E1 (%) | | 10.3 | 9.9 |
| Micronaire | | 4.5 | 4.6 |
| Diseases, Insects and Pests | susceptible = S, moderately susceptible = MS | | |
| Bacterial Blight race 1 | moderately resistant = MR, resistant = R | | |
| Bacterial Blight race 2 | | | |
| Bacterial Blight Race 18 | | | |
| Verticillium Wilt | | | |

TABLE 5-continued

General description of morphological characteristics

| description of characteristic | possible expression/note | Variety | |
|---|---|---|---|
| | | ST 5288B2F | ST 5458B2F |
| Bollworm | | | |
| Cotton Leafworm | | | |
| Fall Armyworm | | | |
| Pink Bollworm | | | |
| Tobacco Budworm | | | |

CITED REFERENCES

Lawrence P. Burdett, "Cotton Variety 02T15," U.S. Pub. No. 20090049564.
F. N. Briggs, and P. F Knowles, 1967: "Introduction to Plant Breeding", Rheinhold Publishing Corporation.
H. F. Sakhanoko et al 2004: "Induction of Somatic embryogenesis and Plant Regeneration in Select Georgia and Pee Dee Cotton Lines", Crop Science 44: 2199-2205.
Umbeck et al 1988: "Genetic engineering of cotton plants and lines", Patent application number EP0290355.
Reynaerts et al 2000: "Improved method for *Agrobacterium* mediated transformation of cotton", Patent application number WO 0071733.
P. Stam, 2003: "Marker-assisted introgression: speed at any cost?" Proceedings of the Eucarpia Meeting on Leafy Vegetable Genetics and Breeding, Noordwijkerhout, The Netherlands, 19-21 Mar. 2003. Eds. Th. J. L. van Hintum, A. Lebeda, D. Pink, J. W. Schut. P 117-124.
Trolinder et al. "Herbicide tolerant cotton plants having event EE-GH1." U.S. Pat. No. 6,818,807 (2004).

The invention claimed is:

1. A seed of cotton variety ST 5288B2F, wherein representative seed of said variety is deposited under ATCC Accession No. PTA-120587.

2. A plant, or a part thereof, produced by growing the seed of claim 1.

3. A plant, or a part thereof, obtained by vegetative reproduction from the plant, or a part thereof, of claim 2, said plant, or a part thereof, having all of the physiological and morphological characteristics of cotton variety ST 5288B2F.

4. A process of vegetative reproduction of cotton variety ST 5288B2F comprising, culturing regenerable cells or tissue from ST 5288B2F, wherein representative seed of said variety is deposited under ATCC Accession No. PTA-120587.

5. A cell or tissue culture produced from the plant, or a part thereof, of claim 2.

6. A cotton plant regenerated from the cell or tissue culture of claim 5, said plant having all of the physiological and morphological characteristics of ST 5288B2F.

7. A method of producing an F1 hybrid cotton seed, comprising the steps of crossing the plant of claim 2 with a different cotton plant and harvesting the resultant F1 hybrid cotton seed.

8. An F1 hybrid cotton seed produced by the method of claim 7.

9. An F1 hybrid cotton plant, or part thereof, produced by growing the hybrid seed of claim 8.

10. A plant obtained by the vegetative reproduction of the cotton plant of claim 9, wherein said plant has all of the physiological and morphological characteristics of the cotton plant of claim 9.

11. A method of producing a cotton seed comprising the steps of crossing the plant of claim 10 with a different cotton plant and harvesting the resultant cotton seed.

12. A method of introducing a desired trait into a cotton plant, the method comprising, transforming the plant of claim 2 with a transgene that confers the desired trait, wherein the transformed plant retains all the physiological and morphological characteristics of cotton variety ST 5288B2F and contains the desired trait.

13. The method of claim 12, wherein said desired trait is fiber quality, herbicide resistance, insect resistance, bacterial disease resistance or fungal disease resistance.

14. A method of introducing a desired trait into a cotton plant, the method comprising transforming the plant of claim 9 with a transgene that confers the desired trait, wherein the transformed plant retains all the physiological and morphological characteristics of the plant of claim 9 and contains the desired trait.

15. A cotton plant produced by the method of claim 12.

16. A method of introducing a single locus conversion into cotton variety ST 5288B2F comprising:

(a) crossing a plant of variety ST 5288B2F, wherein representative seed of variety ST 5288B2F is deposited under ATCC Accession No. PTA 120587, with a second plant comprising a desired single locus to produce F1 progeny plants;

(b) selecting F1 progeny plants that have the single locus to produce selected F1 progeny plants;

(c) crossing the selected progeny plants with at least a first plant of variety ST 5288B2F to produce backcross progeny plants;

(d) selecting backcross progeny plants that have the single locus and physiological and morphological characteristics of cotton variety ST 5288B2F to produce selected backcross progeny plants; and (e) repeating steps (c) and (d) one or more times in succession to produce selected second or higher backcross progeny plants that comprise the single locus and otherwise comprise all of the physiological and morphological characteristics of cotton variety ST 5288B2F when grown in the same environmental conditions.

17. The method of claim 16, wherein the single locus confers a trait selected from the group consisting of male sterility; herbicide tolerance; insect or pest resistance; disease resistance; modified fatty acid metabolism; modified carbohydrate metabolism; and modified cotton fiber characteristics.

\* \* \* \* \*